US006613807B2

(12) United States Patent
Uhrich

(10) Patent No.: US 6,613,807 B2
(45) Date of Patent: *Sep. 2, 2003

(54) THERAPEUTIC POLYANHYDRIDE COMPOUNDS FOR DRUG DELIVERY

(75) Inventor: Kathryn E. Uhrich, Hoboken, NJ (US)

(73) Assignee: Rutgers, The State University of New Jersey, New Brunswick, NJ (US)

(*) Notice: Subject to any disclaimer, the term of this patent is extended or adjusted under 35 U.S.C. 154(b) by 0 days.

This patent is subject to a terminal disclaimer.

(21) Appl. No.: 09/917,231

(22) Filed: Jul. 27, 2001

(65) Prior Publication Data
US 2002/0098161 A1 Jul. 25, 2002

Related U.S. Application Data

(63) Continuation-in-part of application No. 09/627,215, filed on Jul. 27, 2000.

(51) Int. Cl.$^7$ .................. A61K 47/32; A61K 31/195; A61K 31/43; A61K 31/74
(52) U.S. Cl. .................. 514/772.5; 514/197; 514/201; 514/567; 424/78.08
(58) Field of Search .................. 514/772.5, 197, 514/201, 567; 424/428, 427, 78.08, 409, 420

(56) References Cited

U.S. PATENT DOCUMENTS

| | | | |
|---|---|---|---|
| 4,062,855 A | 12/1977 | Allan et al. | 260/295 PA |
| 4,126,445 A | 11/1978 | Allan et al. | 71/94 |
| 4,684,620 A | 8/1987 | Hruby et al. | 514/11 |
| 4,757,128 A | 7/1988 | Domb et al. | 528/271 |
| 4,792,598 A | 12/1988 | Ziegast | 528/206 |
| 4,857,311 A | 8/1989 | Domb et al. | 424/78 |
| 4,868,274 A | 9/1989 | Gupta et al. | 528/206 |
| 4,886,870 A | 12/1989 | D'Amore et al. | 528/206 |
| 4,888,176 A | 12/1989 | Langer et al. | 424/426 |
| 4,891,225 A * | 1/1990 | Langer et al. | 424/428 |
| 4,906,474 A | 3/1990 | Langer et al. | 424/428 |
| 4,938,949 A | 7/1990 | Borch et al. | 424/10 |
| 4,997,904 A | 3/1991 | Domb | 528/206 |
| 4,999,417 A | 3/1991 | Domb | 528/271 |
| 5,082,925 A | 1/1992 | Shalaby et al. | 528/354 |
| 5,175,235 A | 12/1992 | Domb et al. | 528/271 |
| 5,259,968 A | 11/1993 | Emert et al. | 252/51.5 A |
| 5,264,540 A | 11/1993 | Cooper et al. | 528/272 |
| 5,498,729 A | 3/1996 | Domb | 548/500 |
| 5,514,764 A | 5/1996 | Frechet et al. | 528/10 |
| 5,545,409 A | 8/1996 | Laurencin et al. | 424/426 |
| 5,629,009 A | 5/1997 | Laurencin et al. | 424/426 |
| 5,902,110 A | 5/1999 | Alfano et al. | 433/215 |
| 5,902,599 A | 5/1999 | Anseth et al. | 424/426 |
| 5,942,252 A | 8/1999 | Tice et al. | 424/501 |
| 6,071,530 A | 6/2000 | Polson et al. | 424/426 |

FOREIGN PATENT DOCUMENTS

| | | | |
|---|---|---|---|
| DE | 288311 | 3/1991 | A01N/25/10 |
| DE | 288387 | 3/1991 | C08G/67/04 |
| EP | 0246341 | 11/1987 | A61L/27/00 |
| EP | 0 246 341 | * 11/1987 | |
| NL | 9000237 | 8/1991 | A61K/31/60 |
| WO | WO 90/09779 | 9/1990 | A61K/7/16 |
| WO | 91/09831 | * 7/1991 | |
| WO | WO-91/09831 | 7/1991 | C07C/69/035 |
| WO | WO-97/39738 | 10/1997 | A61K/9/16 |
| WO | WO-98/36013 | 8/1998 | C08G/64/00 |
| WO | WO-99/12990 | 3/1999 | C08G/63/00 |
| WO | 99/12990 | * 3/1999 | |
| WO | WO-99/29885 | 6/1999 | C12P/1/00 |

OTHER PUBLICATIONS

Anastasiou, T..J. ,"Novel Polyanhydrides with Enhanced Thermal and Solubility Properties", *Macromolecules, 33* (17), (2000),pp. 6217–6221.

Anastasiou, T..J. ,"Novel, Degradable Polyanhydrides", *25th Annual Meeting Transactions of the Society for Biomaterials*, Abstract,(1999),p, 79, Anastasiou, T..J. ,"Synthesis of Novel, Degradable Polyanhydrides Containing Para–Aminosalicylic Acid as Drug Delivery Devices for Tuberculosis Treatment", *Polymer Preprints, 41*(2), (Aug. 2000),pp. 1366–1367.

Attawia, M..A. ,"Biocompatibility Testing of Poly(anhydride–co–imides) Containing Pyromellitylimidoalanine", *The 21st Annual Meeting of the Society for Biomaterials*, Abstract,(1994),p. 222.

Attawia, M..A. ,"Cytotoxicity testing of poly(anhydride–co–imides) for orthopedic applications", *Journal of Biomedical Materials Research, 29*, (1995),pp. 1233–1240.

Attawia, M..A. ,"In Vitro Bone Biocompatibility of Poly(anhydride–co–imides) Containing Pyromellitylimidoalanine", *Journal of Orthopedic Research, 14*, (1996),pp. 445–454.

Attawia, M..A. ,"Proliferation, Morphology, and Protein Expression by Osteoblasts Cultured on Poly(anhydrideco–amides)", *J. Biomed. Mater. Res. (Appl. Biomater), 48*, (1999), pp. 322–327.

Attawia, M.A. ,"Regional drug delivery with radiation for the treatment of Ewing's sarcoma—In vitro development of a taxol release system", *Journal of Controlled Release, 71*, (2001),pp. 193–202.

Attawia, M..A. ,"The Long Term Osteoblast Response to Poly(anhydride–co–imides); A New Degradable Polymer for Use in Bone", *Proc. of the Fifth World Biomaterials Congress, Toronto, Canada*, (1996),p. 113.

(List continued on next page.)

Primary Examiner—Thurman K. Page
Assistant Examiner—Blessing Fubara
(74) Attorney, Agent, or Firm—Schwegman, Lundberg, Woessner & Kluth, P.A.

(57) ABSTRACT

Polyanhydrides which link low molecular weight drugs containing a carboxylic acid group and an amine, thiol, alcohol or phenol group within their structure into polymeric drug delivery systems are provided. Also provided are methods of producing polymeric drug delivery systems via these polyanhydride linkers as well as methods of administering low molecular weight drugs to a host via the polymeric drug delivery systems.

33 Claims, No Drawings

OTHER PUBLICATIONS

Beaton, M..L. ,"Synthesis of a novel poly(anhydride–ester)", *The Rutgers Scholar—An Electronic Bulletin of Undergraduate Research, 3,* www.rutgersscholar.rutgers.edu/volume03/beatuhri/beatuhri.html,(2001), 7 pgs.

Bedell, C.,"Processing and Hydrolytic Degradation of Aromatic, Ortho–Substituted Polyanhydrides", *Journal of Applied Polymer Science, 80,* (2001),pp. 32–38.

Campo, C..J. ,"Polyanhydrides: the effects of ring substitution changes on polymer properties", *Polymer Bulletin, 42,* (1999), pp. 61–68.

Chafi, N..,"Dosage Form with Salicylic Acid Attached to the Polyanhydride Polymer Dispersed in an Eudragit Matrix", *International Journal of Pharmaceutics, 52,* (1989),pp. 203–211.

Conix, A..,"Aromatic Polyanhydrides, a New Class of High Melting Fiber–Forming Polymers", *Journal of Polymer Science, XXIX,* (1958), pp. 343–353.

Conix, A..,"New High–Melting Fibre–Forming Polymers", *Die Makromolekulare Chemie, XXIV,* (1957), pp. 76–78.

Conix, A..,"Poly[1,3–bis(p–carboxyphenoxy)–Propane anhydride]", *Macromolecular Synthesis, 2,* (1996),pp. 95–99.

Domb, A..J. ,"Synthesis and Characterization of Biodegradable Aromatic Anhydride Copolymers", *Macromolecules, 25,* (1992),pp. 12–17.

Dukovic, G.,"Novel degradable poly(anhydride–esters) for controlled drug release", *The Rutgers Scholar—An Electronic Bulletin of Undergraduate Research, 1,* http://rutgersscholar.rutgers.edu/colume01/uhriduko/uhriduko,html, (1999), 10 pgs.

Erdman, L..,et al. ,"Polymer Prodrugs with Pharmaceutically Active Degradation Products", *Polymer Preprints, 38(2),* (1997),pp. 570–571.

Erdmann, L..,"Chapter 5: Polymeric Prodrugs: Novel Polymers with Bioactive Components", *In: Tailored Polymeric Materials for Controlled Delivery Systems,* I. McCulloch, et al., (Editors), ACS Symposium Series 709, American Chemical Society: Washington, D.C.,(1998),pp. 83–91.

Erdmann, L.,"Degradable poly(anhydride ester) implants: effects of localized salicylic acid release on bone", *Biomaterials, 21,* (2000), pp. 2507–2512.

Erdmann, L..,"Polymeric Prodrugs: Novel Polymers for Delivery of Salicylic Acid", *Annals of Biomedical Engineering, 26 (Suppl. 1),* Abstract No. PB.26, Annual Fall Meeting, (1998),p. S–124.

Erdmann, L..,"Polymeric Salicylic Acid: In Vitro and In Vivo Degradation", *Polymer Preprints, 39(2),* (1998),p. 224–225.

Erdmann, L..,"Synthesis and Characterization of a Polymeric Prodrug", *Proceedings of the American Chemical Society Division of Polymeric Materials: Science and Engineering, 78,* Abstract of Spring Meeting, Dallas, TX,(1998), p. 194.

Erdmann, L..,"Synthesis and degradation characteristics of salicylic acid–derived poly(anhydrid–esters)", *Biomaterials, 21,* (2000),pp. 1941–1946.

Giammona, G..,"Polymeric Prodrugs alpha beta poly–hydroxyethyl–d1–aspartamide as macromolecular carrier for some non–steroidal anti–inflammatory agents", *Abstract from Database BIOSIS Online, Biosciences Information Service, Philadelphia, PA,* Original Publication from the International Journal of Pharmaceutics (Amsterdam), (1989), 1 pg.

Gouin, S..,et al. ,"New Polyanhydrides Made from a Bile Acid Dimer and Sebacic Acid: Synthesis, Characterization, and Degradation", *Macrmolecules, 33,* (2000),pp. 5379–5383.

Ibim. S..,"Controlled Release Based on Poly(anhydride-co–imides)", *Proc. Intern. Symp. Control. Rel. Bioact. Mater., 22,* (1995),2 pgs.

Ibim, S.M. ,"Poly(anhydride–co–imides): In Vivo Biocompatibility in a rat model", *Biomaterials, 19,* (1998),pp. 941–951.

Ibim, S.E. ,"Preliminary In Vivo Report on the Osteocompatibility of Poly(anhydride–co–imides) evaluated in a Tibial Model", *App. Biomater., 43(4),* (1998),pp. 374–379.

Krogh–Jespersen, E.,"Synthesis of a Novel Aromatic Polyanhydride Containing Aminosalicylic Acid", *Polymer Preprints, 41 (1),* (2000), pp. 1048–1049.

Langer, R..,"New Methods of Drug Delivery", *Science, 249,* (Sep. 1990),pp. 1527–1533.

Laurencin, C.T. ,"Poly(andrides–co–imides): In Vivo Biocompatibility Study", *23rd Annual Meeting of the Society for Biomaterials, New Orleans, LA,* (1997), p. 483.

Laurencin, C.T. ,"The Biocompatibility of Poly(anhydride-co–imides): High Strength Polymers for Controlled Drug Delivery", *Proc. 24th Int'l Symp. Control. Rel. Bioact. Mater.,* (1997),pp. 973–974.

Laurencin, C.T. ,"The Bone Biocompatibility of Poly(anhydride–co–imides)—A new generation degradable Polymer for Orthopedic Applications", *41st Annual Meeting of the Orthopedic Research Society, Orlando, FL,* (1995),pp. 143–24.

Laurencin, C.T. ,"The Controlled Delivery of Radiosensitizers: Taxol Treatment of Ewing Sarcoma", *Proc. of the 25th Int'l Symp. Control. Rel. Bioact. Mater.,* (1998),pp. 236–237.

Macedo, B..,et al. ,"The in vivo Response to a Bioactive Biodegadable Polymer", *Journal of Dental Research, 78,* Abstract No. 2827,(1999),p.459.

Macedo, B.,"the In Vivo Response to Bioactive Polyanhydride Monofilament", *Journal of Dental Research, 79 (Abstract No. 3872),* (2000),p. 627.

Pinther, P..,"Synthesis of Polyanhydrides Containing Ester Groups", *Makromol. Chem., Rapid Commun., 11,* (1990),pp. 403–408.

Seidel, J.O. ,"Erosion of Poly(anhydride–co–imides): A Preliminary Mechanistic Study", *J. Appl. Polym. Sci., 62(8),* (1996), pp. 1277–1283.

Shen, E.,"Morphological Characterization of Erodible Polymer Carriers for Drug Release", *Proc. 26th Int'l Symp. Control. Rel. Bioact. Mater.,* (1999),pp. 717–718.

Uhrich, K.E. ,"Chemical Changes during in vivo degradation of poly(anhydride–imide) matrices", *Biomaterials, 19,* (1998),pp. 2045–2050.

Uhrich, K.E. ,"Degradation of poly(anhydride–co–imides): Novel Polymers for Orthopedic Applications", *Mat. Res. Soc. Symp. Proc., 394,* (1995),pp. 41–46.

Uhrich, K.E. ,"In Vitro Degradation Characterisitics of Poly(anhydride–imides) Containing Pyromellitylimidoalanine", *J. Appl. Polymer Sci., Part A, Polym. Chem., 34 (7),* (1996),pp. 1261–1269.

Uhrich, K.E. ,"In Vitro Degradation Characteristics of Poly(anhydride–imides) Containing trimellitylimidoglycine", *J. Appl. Polymer. Sci., 63(11),* (1997),pp. 1401–1411.

Uhrich, K.E., "Poly(anhydride–ester) Degradation: Mechanical Changes and Correlation to Antibiotic Release", *American Chemical Society, Abstracts of Papers Part 2, Abstract No. 121,* 2221st ACS National Meeting, San Diego CA,(2001), 1 pg.

Uhrich, K.E. ,"Synthesis and Characterization of Degradable poly(anhydride–co–imides)", *Macromolecules 28(7),* (1995),pp. 2184–2193.

Uhrich, K.E. ,"Synthesis and Characterization of poly(anhydride–co–imides): Solution Polycondensation of Biodegradable Polymers Derived from Amino Acids", *Proc. of the American Chemical Society, Division of Polymeric Materials: Science and Engineering, 70,* Spring Meeting, San Diego, CA, (1994),pp. 239–240.

Uhrich, K.E. ,"Synthesis of Aminosalicylate–based polyanhydride Prodrugs: Esters, Amides, and Azos", *American Chemical Society, Abstracts of Papers, Part 2, Abstract No. 407,* 222nd ACS National Meeting, Chicago, IL, (2001), 1 pg.

Yazdi, M..,et al. ,"Effects of non–steroidal anti–inflammatory drugs on demineralized bone–induced bone formation", *Journal of Periodontal Research, 27 (1),* (Jan. 1992),pp. 28–33.

* cited by examiner

THERAPEUTIC POLYANHYDRIDE COMPOUNDS FOR DRUG DELIVERY

PRIORITY OF INVENTION

This application is a Continuation-in-Part of U.S. Patent Application Ser. No. 09/627,215, (filed Jul. 27, 2000), which is incorporated herein by reference.

BACKGROUND OF THE INVENTION

Polymers comprising aromatic or aliphatic anhydrides have been studied extensively over the years for a variety of uses. For example, in the 1930s fibers comprising aliphatic polyanhydrides were prepared for use in the textile industry. In the mid 1950s, aromatic polyanhydrides were prepared with improved film and fiber forming properties. More recently, attempts have been made to synthesize polyanhydrides with greater thermal and hydrolytic stability and sustained drug release properties.

U.S. Pat. Nos. 4,757,128 and 4,997,904 disclose the preparation of polyanhydrides with improved sustained drug release properties from pure, isolated prepolymers of diacids and acetic acid. However, these biocompatible and biodegradable aromatic polyanhydrides have radical or aliphatic bonds resulting in compounds with slow degradation times as well as relatively insoluble degradation products unless incorporated into a copolymer containing a more hydrophilic monomer, such as sebacic acid. The aromatic polyanhydrides disclosed in the '128 patent and the '904 patent are also insoluble in most organic solvents. A bioerodible controlled release device produced as a homogenous polymeric matrix from polyanhydrides with aliphatic bonds having weight average molecular weights greater than 20,000 and an intrinsic velocity greater than 0.3 dL/g and a biologically active substance is also described in U.S. Pat. No. 4,888,176. Another bioerodible matrix material for controlled delivery of bioactive compounds comprising polyanhydride polymers with a uniform distribution of aliphatic and aromatic residues is disclosed in U.S. Pat. No. 4,857,311.

Biocompatible and biodegradable aromatic polyanhydrides prepared from para-substituted bis-aromatic dicarboxylic acids for use in wound closure devices are disclosed in U.S. Pat. No. 5,264,540. However, these compounds exhibit high melt and glass transition temperatures and decreased solubility, thus making them difficult to process. The disclosed polyanhydrides also comprise radical or aliphatic bonds which can not be hydrolyzed by water.

Polyanhydride polymeric matrices have also been described for use in orthopedic and dental applications. For example, U.S. Pat. No. 4,886,870 discloses a bioerodible article useful for prosthesis and implantation which comprises a biocompatible, hydrophobic polyanhydride matrix. U.S. Pat. No. 5,902,599 also discloses biodegradable polymer networks for use in a variety of dental and orthopedic applications which are formed by polymerizing anhydride prepolymers.

Biocompatible and biodegradable polyanhydrides have now been developed with improved degradation, processing and solubility properties, as well as utilities based upon their degradation products.

SUMMARY OF THE INVENTION

The present invention provides biocompatible and biodegradable polyanhydrides which serve as the polymeric backbone linking drug molecules into polymeric drug delivery systems. The polyanhydride polymers of the invention demonstrate enhanced solubility and processability, as well as degradation properties due to the use of hydrolyzable bonds such as esters, amides, urethanes, carbamates and carbonates as opposed to radical or aliphatic bonds. The polyanhydride backbone has one or more groups that will provide a therapeutically active compound upon hydrolysis. The polymers of the invention comprise one or more units of formula (I) in the backbone:

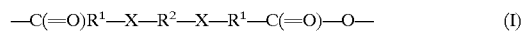

—C(=O)R$^1$—X—R$^2$—X—R$^1$—C(=O)—O—     (I)

wherein each R$^1$ is group that will provide a therapeutically active compound upon hydrolysis of the polymer; each X is independently an amide linkage, a thioester linkage, or an ester linkage; and R$^2$ is a linking group; provided that the therapeutically active compound is not an ortho-hydroxy aryl carboxylic acid.

The polyanhydrides of the invention are used to link low molecular weight drug molecules comprising within their molecular structure one carboxylic acid group and at least one amine, thiol, alcohol or phenol group. Accordingly, polyanhydrides of formula (I) serve as the polymer backbone of polymeric drug delivery systems comprising these low molecular weight drugs.

Thus, the present invention also relates to compositions, methods of producing compositions and methods of using compositions comprising a polyanhydride of Formula (I) and low molecular weight drug molecules containing within their structure one carboxylic acid group and at least one amine, thiol, alcohol or phenol group, wherein molecules of the drug are linked to one another via the polyanhydride. These polymeric drug delivery systems provide an effective means to deliver drugs in a controlled fashion to any site of a host. By "host" it is meant to include both animals and plants.

The invention also provides a pharmaceutical composition comprising a polymer of the invention and a pharmaceutically acceptable carrier.

The invention also provides a therapeutic method for treating a disease in an animal comprising administering to an animal in need of such therapy, an effective amount of a polymer of the invention.

The invention also provides a method of delivering a therapeutically active compound to a host comprising administering to the host a biocompatible and biodegradable polymer of the invention, which degrades into the biologically active compound.

The invention provides a polymer of the invention for use in medical therapy, as well as the use of a polymer of the invention for the manufacture of a medicament useful for the treatment of a disease in a mammal, such as a human.

The invention also provides processes and intermediates disclosed herein that are useful for preparing a polymer of the invention.

DETAILED DESCRIPTION OF THE INVENTION

Definitions

The following definitions are used, unless otherwise described: halo is fluoro, chloro, bromo, or iodo. Alkyl, alkoxy, etc. denote both straight and branched groups; but reference to an individual radical such as "propyl" embraces only the straight chain radical, a branched chain isomer such as "isopropyl" being specifically referred to. Aryl denotes a phenyl radical or an ortho-fused bicyclic carbocyclic radical having about nine to ten ring atoms in which at least one ring is aromatic. Heteroaryl encompasses a radical attached via a ring carbon of a monocyclic aromatic ring containing five or six ring atoms consisting of carbon and one to four heteroatoms each selected from the group consisting of non-peroxide oxygen, sulfur, and N(X) wherein X is absent or is H, O, ($C_1$–$C_6$)alkyl, phenyl or benzyl, as well as a radical of an ortho-fused bicyclic heterocycle of about eight to ten ring atoms derived therefrom, particularly a benz-derivative or one derived by fusing a propylene, trimethylene, or tetramethylene diradical thereto.

The term ester linkage means —OC(=O)— or —C(=O)O—; the term thioester linkage means —SC(=O)— or —C(=O)S—; and the term amide linkage means —N(R)C(=O)— or —C(=O)N(R)—, wherein each R is a suitable organic radical, such as, for example, hydrogen, ($C_1$–$C_6$)alkyl, ($C_3$–$C_6$)cycloalkyl, ($C_3$–$C_6$)cycloalkyl($C_1$–$C_6$)alkyl, aryl, heteroaryl, aryl($C_1$–$C_6$)alkyl, or heteroaryl($C_1$–$C_6$)alkyl. The term urethane or carbamate linkage means —OC(=O)N(R)— or —N(R)C(=O)O—, wherein each R is a suitable organic radical, such as, for example, hydrogen, ($C_1$–$C_6$)alkyl, ($C_3$–$C_6$)cycloalkyl, ($C_3$–$C_6$)cycloalkyl($C_1$–$C_6$)alkyl, aryl, heteroaryl, aryl($C_1$–$C_6$)alkyl, or heteroaryl($C_1$–$C_6$)alkyl, and the term carbonate linkage means —OC(=O)O—.

The term "amino acid," comprises the residues of the natural amino acids (e.g. Ala, Arg, Asn, Asp, Cys, Glu, Gln, Gly, His, Hyl, Hyp, Ile, Leu, Lys, Met, Phe, Pro, Ser, Thr, Trp, Tyr, and Val) in D or L form, as well as unnatural amino acids (e.g. phosphoserine, phosphothreonine, phosphotyrosine, hydroxyproline, gamma-carboxyglutamate; hippuric acid, octahydroindole-2-carboxylic acid, statine, 1,2,3,4,-tetrahydroisoquinoline-3-carboxylic acid, penicillamine, ornithine, citruline, α-methyl-alanine, para-benzoylphenylalanine, phenylglycine, propargylglycine, sarcosine, and tert-butylglycine). The term also comprises natural and unnatural amino acids bearing a conventional amino protecting group (e.g. acetyl or benzyloxycarbonyl), as well as natural and unnatural amino acids protected at the carboxy terminus (e.g. as a ($C_1$–$C_6$)alkyl, phenyl or benzyl ester or amide; or as an α-methylbenzyl amide). Other suitable amino and carboxy protecting groups are known to those skilled in the art (See for example, Greene, T. W.; Wutz, P. G. M. "Protecting Groups In Organic Synthesis" second edition, 1991, New York, John Wiley & sons, Inc., and references cited therein).

The term "host" includes animals and plants.

The term "peptide" describes a sequence of 2 to 35 amino acids (e.g. as defined hereinabove) or peptidyl residues. The sequence may be linear or cyclic. For example, a cyclic peptide can be prepared or may result from the formation of disulfide bridges between two cysteine residues in a sequence. Preferably a peptide comprises 3 to 20, or 5 to 15 amino acids. Peptide derivatives can be prepared as disclosed in U.S. Pat. Nos. 4,612,302; 4,853,371; and 4,684,620, or as described in the Examples hereinbelow. Peptide sequences specifically recited herein are written with the amino terminus on the left and the carboxy terminus on the right.

Polymers of the Invention

The biocompatible, biodegradable polyanhydrides of the invention are useful in a variety of applications where delivery of a biologically active compound is desired. Examples of such applications include, but are not limited to, medical, dental and cosmetic uses.

The polymers of the invention may be prepared in accordance with methods commonly employed in the field of synthetic polymers to produce a variety of useful products with valuable physical and chemical properties. The polymers can be readily processed into pastes or solvent cast to yield films, coatings, microspheres and fibers with different geometric shapes for design of various medical implants, and may also be processed by compression molding and extrusion.

Medical implant applications include the use of polyanhydrides to form shaped articles such as vascular grafts and stents, bone plates, sutures, implantable sensors, implantable drug delivery devices, stents for tissue regeneration, and other articles that decompose into non-toxic components within a known time period.

Polymers of the present invention can also be incorporated into oral formulations and into products such as skin moisturizers, cleansers, pads, plasters, lotions, creams, gels, ointments, solutions, shampoos, tanning products and lipsticks for topical application.

Although the invention provides homopolymers that are prepared from suitably functionalized biologically active compounds, Applicant has discovered that the mechanical and hydrolytic properties of polymers comprising one or more biologically active compounds can be controlled by modifying the linking group ($R^2$) in the polymer backbone.

Preferably, the polymers of the invention comprise backbones wherein biologically active compounds and linker groups ($R^2$) are bonded together through ester linkages, thioester linkages, amide linkages, or a mixture thereof. Due to the presence of the ester, thioester, and/or amide linkages, the polymers can be hydrolyzed under physiological conditions to provide the biologically active compounds. Thus, the polymers of the invention can be particularly useful as a controlled release source for a biologically active compound, or as a medium for the localized delivery of a biologically active compound to a selected site. For example, the polymers of the invention can be used for the localized delivery of a therapeutic agent to a selected site within the body of a human patient (i.e. within or near a tumor), where the degradation of the polymer provides localized, controlled, release of the therapeutic agent.

Biodegradable, biocompatible polyanhydrides which serve as linkers for low molecular weight drug molecules have now been developed. Compositions comprising low molecular weight drugs linked via polyanhydrides of the present invention are useful in a variety of applications wherein delivery of the drugs in a controlled fashion is desired. For purposes of the present invention, by "low molecular weight drug" it is meant to include any compound with one carboxylic acid group and at least one amine, thiol, alcohol or phenol group within its structure, wherein the compound has a demonstrated pharmacological activity and a molecular weight of approximately 1000 daltons or less.

In one embodiment, polyanhydrides of the present invention are prepared by the method described in Conix, Macromol. Synth., 2, 95–99 (1996). In this method, dicarboxylic acids are acetylated in an excess of acetic anhydride at reflux temperatures followed by melt condensation of the resulting carboxylic acid anhydride at 180° C. for 2–3 hours. The resulting polymers are isolated by precipitation into diethylether from methylene chloride. The described process is essentially the conventional method for polymerizing bisaromatic dicarboxylic acid anhydrides into aromatic polyanhydrides.

Polyanhydrides of the present invention have average molecular weights ranging between about 1500 daltons up to about 100,000 daltons, up to about 100,000 daltons, calculated by Gel Permeation Chromatography (GPC) relative to narrow molecular weight polystyrene standards. Preferred aromatic polyanhydrides have average molecular weights of about 1500 daltons, up to about 50,000 daltons calculated by Gel Permeation Chromatography (GPC) relative to narrow molecular weight polystyrene standards. Preferred azopolymers have average molecular weights of about 1500 daltons, up to about 35,000 daltons.

Biologically Active Compounds

It has been found that the polyanhydride compounds of the invention can serve as a polymer backbone for degradable polymeric drug delivery systems for a multitude of low molecular weight drugs. Drugs which can be linked into degradable copolymers via the polyanhydrides have the following characteristics. The drugs have a relatively low molecular weights of approximately 1,000 daltons or less. The drug must contain within its molecular structure one carboxylic acid group. In addition, the drug must contain at least one carboxylic acid (—COOH), amine (—NHR), thiol (—SH), alcohol (—OH) or phenol (—Ph—OH) group within its structure.

The term "biologically active compound" includes therapeutic agents that provide a therapeutically desirable effect when administered to an animal (e.g., a mammal, such as a human). Therapeutic agents that can be incorporated into the polymers of the invention include suitably functionalized analgesics, anesthetics, anti-Parkinson's agents, anti-infectives, antiacne agents, antibiotics, anticholinergics, anticoagulants, anticonvulsants, antidiabetic agents, antidyskinetics, antifibrotic agents, antifibrotics, antifungal agents, antiglaucoma agents, anti-inflammatory agents, antineoplastics, antiosteoporotics, antipagetics, antisporatics, antipyretics, antiseptics/disinfectants, antithrombotics, bone resorption inhibitors, calcium regulators, cardioprotective agents, cardiovascular agents, central nervous system stimulants, cholinesterase inhibitors, contraceptives, deodorants, dopamine receptor agonists, erectile dysfunction agents, fertility agents, gastrointestinal agents, gout agents, hormones, hypnotics, immunomodulators, immunosuppressives, keratolytics, migraine agents, motion sickness agents, muscle relaxants, nucleoside analogs, obesity agents, ophthalmic agents, osteoporosis agents, parasympatholytics, parasympathomimetics, prostaglandins, psychotherapeutic agents, respiratory agents, sclerosing agents, sedatives, skin and mucous membrane agents, smoking cessation agents, sympatholytics, synthetic antibacterial agents, ultraviolet screening agents, urinary tract agents, vaginal agents, and vasodilators (see Physicians' Desk Reference, 55 ed., 2001, Medical Economics Company, Inc., Montvale, N.J., pages 201–202).

In a preferred embodiment, suitable examples of low molecular weight drugs with the required functional groups within their structure can be found in almost all classes of drugs including, but not limited to, analgesics, anesthetics, antiacne agents, antibiotics, synthetic antibacterial agents, anticholinergics, anticoagulants, antidyskinetics, antifibrotics, antifungal agents, antiglaucoma agents, anti-inflammatory agents, antineoplastics, antiosteoporotics, antipagetics, anti-Parkinson's agents, antisporatics, antipyretics, antiseptics/disinfectants, antithrombotics, bone resorption inhibitors, calcium regulators, keratolytics, sclerosing agents and ultraviolet screening agents.

The biologically active compounds can also comprise other functional groups (including hydroxy groups, mercapto groups, amine groups, and carboxylic acids, as well as others) that can be used to modify the properties of the polymer (e.g. for branching, for cross linking, for appending other molecules (e.g. another biologically active compound) to the polymer, for changing the solubility of the polymer, or for effecting the biodistribution of the polymer). Lists of therapeutic agents can be found, for example, in: Physicians' Desk Reference, 55 ed., 2001, Medical Economics Company, Inc., Montvale, N.J.; USPN Dictionary of USAN and International Drug Names, 2000, The United States Pharmacopeial Convention, Inc., Rockville, Md.; and The Merck Index, 12 ed., 1996, Merck & Co., Inc., Whitehouse Station, N.J. One skilled in the art can readily select therapeutic agents that possess the necessary functional groups for incorporation into the polymers of the invention from these lists.

Examples of anti-bacterial compounds suitable for use in the present invention include, but are not limited to, 4-sulfanilamidosalicylic acid, acediasulfone, amfenac, amoxicillin, ampicillin, apalcillin, apicycline, aspoxicillin, aztreonam, bambermycin(s), biapenem, carbenicillin, carumonam, cefadroxil, cefamandole, cefatrizine, cefbuperazone, cefclidin, cefdinir, cefditoren, cefepime, cefetamet, cefixime, cefinenoxime, cefminox, cefodizime, cefonicid, cefoperazone, ceforanide, cefotaxime, cefotetan, cefotiam, cefozopran, cefpimizole, cefpiramide, cefpirome, cefprozil, cefroxadine, ceftazidime, cefteram, ceftibuten, ceftriaxone, cefuzonam, cephalexin, cephaloglycin, cephalosporin C, cephradine, ciprofloxacin, clinafloxacin, cyclacillin, enoxacin, epicillin, flomoxef, grepafloxacin, hetacillin, imipenem, lomefloxacin, lymecycline, meropenem, moxalactam, mupirocin, nadifloxacin, norfloxacin, panipenem, pazufloxacin, penicillin N, pipemidic acid, quinacillin, ritipenem, salazosulfadimidine, sparfloxacin, succisulfone, sulfachrysoidine, sulfaloxic acid, teicoplanin, temafloxacin, temocillin, ticarcillin, tigemonam, tosufloxacin, trovafloxacin, vancomycin, and the like.

Examples of anti-fungal compounds suitable for use in the present invention include, but are not limited to amphotericin B, azaserine, candicidin(s), lucensomycin, natamycin, nystatin, and the like.

Examples of anti-neoplastic compounds suitable for use in the present invention include, but are not limited to 6-diazo-5-oxo-L-norleucine, azaserine, carzinophillin A, denopterin, edatrexate, eflomithine, melphalan, methotrexate, mycophenolic acid, podophyllinic acid 2-ethylhydrazide, pteropterin, streptonigrin, Tomudex® (N-((5-(((1,4-Dihydro-2-methyl-4-oxo-6-quinazolinyl)methyl) methylamino)-2-thienyl)carbonyl)-L-glutamic acid), ubenimex, and the like.

Examples of anti-thrombotic compounds for use in the present invention include, but are not limited to, argatroban, iloprost, lamifiban, taprostene, tirofiban and the like.

Examples of immunosuppressive compounds suitable for use in the present invention include, but are not limited to bucillamine, mycophenolic acid, procodazole, romurtide, ubenimex and the like.

Examples of NSAID compounds suitable for use in the present invention include, but are not limited to 3-amino-4-hydroxybutyric acid, aceclofenac, alminoprofen, bromfenac, bumadizon, carprofen, diclofenac, diflunisal, enfenamic acid, etodolac, fendosal, flufenamic acid, gentisic acid, meclofenamic acid, mefenamic acid, mesalamine, niflumic acid, olsalazine oxaceprol, S-adenosylmethionine, salicylic acid, salsalate, sulfasalazine, tolfenamic acid, and the like.

Linking Group "$R^2$"

The nature of the linking group "$R^2$" in a polymer of the invention is not critical provided the polymer of the invention possesses acceptable mechanical properties and release kinetics for the selected therapeutic application. The linking group $R^2$ is typically a divalent organic radical having a molecular weight of from about 25 daltons to about 400 daltons. More preferably, $R^2$ has a molecular weight of from about 40 daltons to about 200 daltons.

The linking group $R^2$ typically has a length of from about 5 angstroms to about 100 angstroms using standard bond lengths and angles. More preferably, the linking group L has a length of from about 10 angstroms to about 50 angstroms.

The linking group may be biologically inactive, or may itself possess biological activity. The linking group can also comprise other functional groups (including hydroxy groups, mercapto groups, amine groups, carboxylic acids, as well as others) that can be used to modify the properties of the polymer (e.g. for branching, for cross linking, for appending other molecules (e.g. another biologically active compound) to the polymer, for changing the solubility of the polymer, or for effecting the biodistribution of the polymer).

Specific And Preferred Values

Specific and preferred values listed herein for radicals, substituents, groups, and ranges, are for illustration only; they do not exclude other defined values or other values within defined ranges for the radicals and substituents.

Specifically, $(C_1-C_6)$alkyl can be methyl, ethyl, propyl, isopropyl, butyl, isobutyl, sec-butyl, pentyl, 3-pentyl, or hexyl; $(C_3-C_6)$cycloalkyl can be cyclopropyl, cyclobutyl, cyclopentyl, or cyclohexyl; $(C_3-C_6)$cycloalkyl$(C_1-C_6)$alkyl can be cyclopropylmethyl, cyclobutylmethyl, cyclopentylmethyl, cyclohexylmethyl, 2-cyclopropylethyl, 2-cyclobutylethyl, 2-cyclopentylethyl, or 2-cyclohexylethyl; $(C_1-C_6)$alkoxy can be methoxy, ethoxy, propoxy, isopropoxy, butoxy, iso-butoxy, sec-butoxy, pentoxy, 3-pentoxy, or hexyloxy; $(C_1-C_6)$alkanoyl can be acetyl, propanoyl or butanoyl; $(C_1-C_6)$alkoxycarbonyl can be methoxycarbonyl, ethoxycarbonyl, propoxycarbonyl, isopropoxycarbonyl, butoxycarbonyl, pentoxycarbonyl, or hexyloxycarbonyl; $(C_1-C_6)$alkylthio can be methylthio, ethylthio, propylthio, isopropylthio, butylthio, isobutylthio, pentylthio, or hexylthio; $(C_2-C_6)$alkanoyloxy can be acetoxy, propanoyloxy, butanoyloxy, isobutanoyloxy, pentanoyloxy, or hexanoyloxy; aryl can be phenyl, indenyl, or naphthyl; and heteroaryl can be furyl, imidazolyl, triazolyl, triazinyl, oxazoyl, isoxazoyl, thiazolyl, isothiazoyl, pyrazolyl, pyrrolyl, pyrazinyl, tetrazolyl, pyridyl, (or its N-oxide), thienyl, pyrimidinyl (or its N-oxide), indolyl, isoquinolyl (or its N-oxide) or quinolyl (or its N-oxide).

A specific biologically active compound that can be incorporated into the polymers of the invention is 3-amino-4-hydroxybutyric acid, 6-diazo-5-oxo-L-norleucine, aceclofenac, acediasulfone, alminoprofen, amfenac, amoxicillin, amphotericin B, ampicillin, apalcillin, apicycline, aspoxicillin, azaserine, aztreonam, bambermycin (s), biapenem, bromfenac, bucillamine, bumadizon, candicidin(s), carbenicillin, carprofen, carumonam, carzinophillin A, cefadroxil, cefamandole, cefatrizine, cefbuperazone, cefclidin, cefdinir, cefditoren, cefepime, cefetamet, cefixime, cefinenoxime, cefminox, cefodizime, cefonicid, cefoperazone, cefforanide, cefotaxime, cefotetan, cefotiam, cefozopran, cefpimizole, cefpiramide, cefpirome, cefprozil, cefroxadine, ceftazidime, cefteram, ceftibuten, ceftriaxone, cefuzonam, cephalexin, cephaloglycin, cephalosporin C, cephradine, ciprofloxacin, clinafloxacin, cyclacillin, denopterin, diclofenac, edatrexate, eflomithine, enfenamic acid, enoxacin, epicillin, etodolac, flomoxef, flufenamic acid, grepafloxacin, hetacillin, imipenem, lomefloxacin, lucensomycin, lymecycline, meclofenamic acid, mefenamic acid, melphalan, meropenem, methotrexate, moxalactam, mupirocin, mycophenolic acid, mycophenolic acid, nadifloxacin, natamycin, niflumic acid, norfloxacin, nystatin, oxaceprol, panipenem, pazufloxacin, penicillin N, pipemidic acid, podophyllinic acid 2-ethylhydrazide, procodazole, pteropterin, quinacillin, ritipenem, romurtide, S-adenosylmethionine, salazosulfadimidine, sparfloxacin, streptonigrin, succisulfone, sulfachrysoidine, sulfaloxic acid, teicoplanin, temafloxacin, temocillin, ticarcillin, tigemonam, tolfenamic acid, Tomudex® (N-((5-(((1,4-Dihydro-2-methyl-4-oxo-6-quinazolinyl)methyl)methylamino)-2-thienyl)carbonyl)-L-glutamic acid), tosufloxacin, trovafloxacin, ubenimex or vancomycin.

Another specific value for $R^2$ is a divalent, branched or unbranched, saturated or unsaturated, hydrocarbon chain, having from 1 to 20 carbon atoms, wherein the chain is optionally substituted on carbon with one or more (e.g. 1, 2, 3, or 4) substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy.

Another specific value for $R^2$ is an amino acid.

Another specific value for $R^2$ is a peptide.

Another specific value for $R^2$ is a divalent, branched or unbranched, saturated or unsaturated, hydrocarbon chain, having from 1 to 20 carbon atoms, wherein one or more (e.g. 1, 2, 3, or 4) of the carbon atoms is optionally replaced by (—O—) or (—NR—).

A more specific value for $R^2$ is a divalent, branched or unbranched, saturated or unsaturated, hydrocarbon chain, having from 3 to 15 carbon atoms, wherein one or more (e.g. 1, 2, 3, or 4) of the carbon atoms is optionally replaced by (—O—) or NR—), and wherein the chain is optionally substituted on carbon with one or more (e.g. 1, 2, 3, or 4) substituents selected from the group consisting of $(C_1-C_6)$alkoxy, $(C_3-C_6)$cycloalkyl, $(C_1-C_6)$alkanoyl, $(C_1-C_6)$alkanoyloxy, $(C_1-C_6)$alkoxycarbonyl, $(C_1-C_6)$alkylthio, azido, cyano, nitro, halo, hydroxy, oxo, carboxy, aryl, aryloxy, heteroaryl, and heteroaryloxy.

Another more specific value for $R^2$ is a divalent, branched or unbranched, saturated or unsaturated, hydrocarbon chain, having from 3 to 15 carbon atoms, wherein one or more (e.g. 1, 2, 3, or 4) of the carbon atoms is optionally replaced by (—O—) or (—NR—).

Another more specific value for $R^2$ is a divalent, branched or unbranched, saturated or unsaturated, hydrocarbon chain, having from 3 to 15 carbon atoms.

Another more specific value for $R^2$ is a divalent, branched or unbranched, hydrocarbon chain, having from 3 to 15 carbon atoms.

A preferred value for $R^2$ is a divalent, branched or unbranched, hydrocarbon chain, having from 6 to 10 carbon atoms.

A more preferred value for $R^2$ is a divalent hydrocarbon chain having 7, 8, or 9 carbon atoms.

A most preferred value for $R^2$ is a divalent hydrocarbon chain having 8 carbon atoms.

A specific polyanhydride linker of the present invention comprises the structure of formula (I):

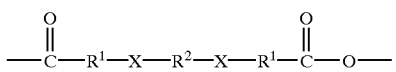

wherein $R^1$ is selected from the group consisting of alkyls, cycloalkyls, substituted alkyls, aromatics, substituted aromatics, lactams, and lactones; X is selected from the group consisting of amides, thioamides, esters and thioesters; and $R^2$ is an alkyl represented by $—(CH_2)_n—$ wherein n is from 1 to 20.

A specific polyanhydride polymer of the present invention includes biologically active compounds provided that the biologically active compound is not an alpha-hydroxy carboxylic acid.

A specific polyanhydride polymer of the present invention includes biologically active compounds provided that the biologically active compound is not an ortho-hydroxy aryl carboxylic acid.

Such a polymer, wherein each $R^1$ is a group that will provide a different biologically active compound upon hydrolysis of the polymer, are particularly useful for the administration of a combination of two therapeutic agents to an animal.

A preferred group of polyanhydride compounds includes polymers that are comprised of compounds containing at least one free carboxylic acid group, and at least one alcohol group, carboxylic acid or amine group available for reactions which can self-polymerize or co-polymerize with carboxylic acid, alcohol or amine groups or bis(acyl) chlorides.

Formulations

The polymers of the invention can be formulated as pharmaceutical compositions and administered to a mammalian host, such as a human patient in a variety of forms adapted to the chosen route of administration, i.e., orally, rectally, or parenterally, by intravenous, intramuscular, intraperitoneal, intraspinal, intracranial, topical, ocular or subcutaneous routes. For some routes of administration, the polymer can conveniently be formulated as micronized particles.

Thus, the present compounds may be systemically administered, e.g., orally, in combination with a pharmaceutically acceptable vehicle such as an inert diluent or an assimilable edible carrier. They may be enclosed in hard or soft shell gelatin capsules, may be compressed into tablets, or may be incorporated directly with the food of the patient's diet. For oral therapeutic administration, the active compound may be combined with one or more excipients and used in the form of ingestible tablets, buccal tablets, troches, capsules, elixirs, suspensions, syrups, wafers, and the like. Such compositions and preparations preferably contain at least 0.1% of polymer by weight. The percentage of the compositions and preparations may, of course, be varied and may conveniently be between about 2 to about 80% of the weight and preferably 2 to about 60% of a given unit dosage form. The amount of polymer in such therapeutically useful compositions is such that an effective dosage level will be obtained.

The tablets, troches, pills, capsules, and the like may also contain the following: binders such as gum tragacanth, acacia, corn starch or gelatin; excipients such as dicalcium phosphate; a disintegrating agent such as corn starch, potato starch, alginic acid and the like; a lubricant such as magnesium stearate; and a sweetening agent such as sucrose, fructose, lactose or aspartame or a flavoring agent such as peppermint, oil of wintergreen, or cherry flavoring may be added. When the unit dosage form is a capsule, it may contain, in addition to materials of the above type, a liquid carrier, such as a vegetable oil or a polyethylene glycol. Various other materials may be present as coatings or to otherwise modify the physical form of the solid unit dosage form. For instance, tablets, pills, or capsules may be coated with gelatin, wax, shellac or sugar and the like. A syrup or elixir may contain the active compound, sucrose or fructose as a sweetening agent, methyl and propylparabens as preservatives, a dye and flavoring such as cherry or orange flavor. Of course, any material used in preparing any unit dosage form should be pharmaceutically acceptable and substantially non-toxic in the amounts employed. In addition, the active compound may be incorporated into sustained-release preparations and devices.

The polymer may also be administered intravenously, intraspinal, intracranial, or intraperitoneally by infusion or injection. Solutions of the polymer can be prepared a suitable solvent such as an alcohol, optionally mixed with a nontoxic surfactant. Dispersions can also be prepared in glycerol, liquid polyethylene glycols, triacetin, and mixtures thereof and in oils. Under ordinary conditions of storage and use, these preparations contain a preservative to prevent the growth of microorganisms.

The pharmaceutical dosage forms suitable for injection or infusion can include sterile solutions or dispersions or sterile powders comprising the polymer containing the active ingredient which are adapted for the extemporaneous preparation of sterile injectable or infusible solutions or dispersions, optionally encapsulated in liposomes. In all cases, the ultimate dosage form should be sterile, fluid and stable under the conditions of manufacture and storage. The liquid carrier or vehicle can be a solvent or liquid dispersion medium comprising, for example, ethanol, a polyol (for example, glycerol, propylene glycol, liquid polyethylene glycols, and the like), vegetable oils, nontoxic glyceryl esters, and suitable mixtures thereof. The proper fluidity can be maintained, for example, by the formation of liposomes, by the maintenance of the required particle size in the case of dispersions or by the use of surfactants. The prevention of the action of microorganisms can be brought about by various antibacterial and antifungal agents, for example, parabens, chlorobutanol, phenol, sorbic acid, thimerosal, and the like. In many cases, it will be preferable to include isotonic agents, for example, sugars, buffers or sodium chloride. Prolonged absorption of the injectable compositions can be brought about by the use in the compositions of agents delaying absorption, for example, aluminum monostearate and gelatin.

Sterile injectable solutions are prepared by incorporating the polymer in the required amount in the appropriate solvent with various of the other ingredients enumerated above, as required, followed by filter sterilization. In the case of sterile powders for the preparation of sterile injectable solutions, the preferred methods of preparation are vacuum drying and the freeze drying techniques, which yield a powder of the active ingredient plus any additional desired ingredient present in the previously sterile-filtered solutions.

For topical administration, the present polymers can be applied in pure form. However, it will generally be desirable to administer them as compositions or formulations, in combination with a dermatologically acceptable carrier, which may be a solid or a liquid.

Useful solid carriers include finely divided solids such as talc, clay, microcrystalline cellulose, silica, alumina and the like. Useful liquid carriers include, alcohols or glycols or alcohol/glycol blends, in which the present compounds can be dissolved or dispersed at effective levels, optionally with the aid of non-toxic surfactants. Adjuvants such as fragrances and additional antimicrobial agents can be added to optimize the properties for a given use. The resultant liquid compositions can be applied from absorbent pads, used to impregnate bandages and other dressings, or sprayed onto the affected area using pump-type or aerosol sprayers.

Thickeners such as synthetic polymers, fatty acids, fatty acid salts and esters, fatty alcohols, modified celluloses or modified mineral materials can also be employed with liquid carriers to form spreadable pastes, gels, ointments, soaps, and the like, for application directly to the skin of the user.

Examples of useful dermatological compositions which can be used to deliver the polymers of the invention to the skin are known to the art; for example, see Jacquet et al. (U.S. Pat. No. 4,608,392), Geria (U.S. Pat. No. 4,992,478), Smith et al. (U.S. Pat. No. 4,559,157) and Wortzman (U.S. Pat. No. 4,820,508).

Dosages

Useful dosages of the polymers can be determined by comparing their in vitro activity, and in vivo activity of the therapeutic agent in animal models. Methods for the extrapolation of effective dosages in mice, and other animals, to humans are known to the art; for example, see U.S. Pat. No. 4,938,949. Additionally, useful dosages can be determined by measuring the rate of hydrolysis for a given polymer under various physiological conditions. The amount of a polymer required for use in treatment will vary not only with the particular polymer selected but also with the route of administration, the nature of the condition being treated and the age and condition of the patient and will be ultimately at the discretion of the attendant physician or clinician.

The desired dose may conveniently be presented in a single dose or as divided doses administered at appropriate intervals, for example, as two, three, four or more sub-doses per day. The sub-dose itself may be further divided, e.g., into a number of discrete loosely spaced administrations.

Combination Therapies

The polymers of the invention are also useful for administering a combination of therapeutic agents to an animal. Such a combination therapy can be carried out in the following ways: 1) a second therapeutic agent can be dispersed within the polymer matrix of a polymer of the invention, and can be released upon degradation of the polymer; 2) a second therapeutic agent can be appended to a polymer of the invention (i.e. not in the backbone of the polymer) with bonds that hydrolyze to release the second therapeutic agent under physiological conditions; 3) the polymer of the invention can incorporate two therapeutic agents into the polymer backbone (e.g. a polymer comprising one or more units of formula (I)) or 4) two polymers of the invention, each with a different therapeutic agent can be administered together (or within a short period of time).

Thus, the invention also provides a pharmaceutical composition comprising a polymer of the invention and a second therapeutic agent that is dispersed within the polymer matrix of a polymer of the invention. The invention also provides a pharmaceutical composition comprising a polymer of the invention having a second therapeutic agent appended to the polymer (e.g. with bonds that will hydrolyze to release the second therapeutic agent under physiological conditions).

The polymers of the invention can also be administered in combination with other therapeutic agents that are effective to treat a given condition to provide a combination therapy. Thus, the invention also provides a method for treating a disease in a mammal comprising administering an effective amount of a combination of a polymer of the invention and another therapeutic agent. The invention also provides a pharmaceutical composition comprising a polymer of the invention, another therapeutic agent, and a pharmaceutically acceptable carrier.

Preparation of Polymers of the Invention

Processes for preparing polyanhydride polymers of the invention are provided as further embodiments of the invention and are illustrated by the following procedures in which the meanings of the generic radicals are as given above unless otherwise qualified.

For example, a polymer of the invention can be prepared, as illustrated in Scheme I, from a biologically active compound of formula ($Z_1$—$R^1$—$Z_2$) and a linker precursor of formula $Y^1$—$R^2$—$Y_2$, wherein one of $Z_1$ and $Z_2$ is a carboxylic acid group and the other groups $Y_1$, $Y_2$, $Z_1$, and $Z_2$ are independently selected from the values in the table below.

Scheme I $$2 Z_2\text{—}R^1\text{—}Z_1 + Y_1\text{—}R^2\text{—}Y_2 \longrightarrow$$

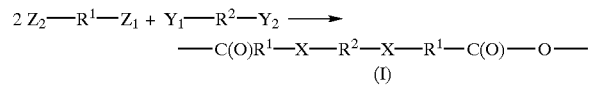

The biologically active compound and the linker precursor can be polymerized using well known synthetic techniques (e.g. by condensation) to provide a polymer of the invention (I) wherein each X is independently an ester linkage, a thioester linkage, or an amide linkage.

Depending on the reactive functional group ($Z_1$, and $Z_2$) of the biologically active compound, a corresponding functional group ($Y_1$ or $Y_2$) can be selected from the following table, to provide an ester linkage, thioester linkage, or amide linkage in the polymer backbone.

| Functional Group On Biologically active compound ($Z_1$ or $Z_2$) | Functional Group On Linker Precursor ($Y_1$ or $Y_2$) | Resulting Linkage In Polymer |
|---|---|---|
| —COOH | —OH | Ester |
| —COOH | —NHR | Amide |
| —COOH | —SH | Thioester |
| —OH | —COOH | Ester |
| —SH | —COOH | Thioester |
| —NHR | —COOH | Amide |

As will be clear to one skilled in the art, suitable protecting groups can be used during the reaction illustrated in Scheme I (and in the reactions illustrated in Schemes II–XV below). For example, other functional groups present in the biologically active compound or the linker precursor can be protected during polymerization, and the protecting groups can subsequently be removed to provide the polymer of the invention. Suitable protecting groups and methods for their incorporation and removal are well known in the art (see for example Greene, T. W.; Wutz, P. G. M. "Protecting Groups In Organic Synthesis" second edition, 1991, New York, John Wiley & sons, Inc.).

Additionally, when a carboxylic acid is reacted with a hydroxy group, a mercapto group, or an amine group to provide an ester linkage, thioester linkage, or an amide linkage, the carboxylic acid can be activated prior to the reaction, for example, by formation of the corresponding acid chloride. Numerous methods for activating carboxylic acids, and for preparing ester linkages, thioester linkages, and amide linkages, are known in the art (see for example Advanced Organic Chemistry: Reaction Mechanisms and Structure, 4 ed., Jerry March, John Wiley & Sons, pages 419–437 and 1281).

A polyanhydride/polyester of the invention can be formed from a hydroxy/carboxylic acid containing compound of formula (HOOC—$R^1$—OH) and from a linker precursor of formula HOOC—$R^2$—COOH as illustrated in Scheme 2.

SCHEME 2

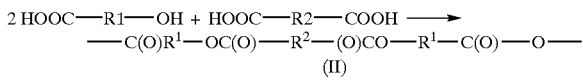

(II)

A polyanhydride/polyamide of the invention can be prepared using a procedure similar to that illustrated in Scheme 2 by replacing the biologically active hydroxy/carboxylic acid compound in Scheme 2 with a suitable biologically active amine/carboxylic acid compound.

A polyanhydride/polythioester of the invention can be prepared using a procedure similar to that illustrated in Scheme 2 by replacing the biologically active hydroxy/carboxylic acid compound in Scheme 2 with a suitable mercapto/carboxylic acid compound.

Alternatively, a polyanhydride/polyester of the invention can be formed from a dicarboxylic acid containing compound of formula HOOC—$R^1$—COOH and from a diol linker precursor of formula (HO—$R^2$—OH) as illustrated in Scheme 3.

SCHEME 3

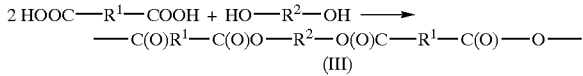

(III)

A polyanhydride/polyamide of the invention can be prepared using a procedure similar to that illustrated in Scheme 2 by replacing the diol linker compound in Scheme 3 with a suitable diamine compound.

A polyanhydride/polythioester of the invention can be prepared using a procedure similar to that illustrated in Scheme 2 by replacing the diol linker compound in Scheme 3 with a suitable dimercapto compound.

Other polymers of the invention can be formed using the reactions described herein, using starting materials that have suitable groups to prepare the desired polymer.

Polymeric drug delivery systems of the present invention can be characterized by proton nuclear magnetic resonance (NMR) spectroscopy, infrared (IR) spectroscopy, gel permeation chromatography (GPC), high performance liquid chromatography (HPLC), differential scanning calorimetry (DSC), and thermal gravimetric analysis (TGA). For infrared spectroscopy, samples are prepared by solvent casting on NaCl plates. $^1$H and $^{13}$C NMR spectroscopy is obtained in solutions of CDCl$_3$ or DMSO-d$_6$ with solvent as the internal reference.

GPC is performed to determine molecular weight and polydispersity. In this method, samples are dissolved in tetrahydrofuran and eluted through a mixed bed column (PE PL gel, 5 µm mixed bed) at a flow rate of 0.5 mL/minute. It is preferred that the samples (about 5 mg/mL) be dissolved into the tetrahydrofuran and filtered using 0.5 µm PTFE syringe filters prior to column injection. Molecular weights are determined relative to narrow molecular weight polystyrene standards (Polysciences, Inc.).

Thermal analysis can also be performed using a system such as the Perkin-Elmer system consisting of a TGA 7 thermal gravimetric analyzer equipped with PE AD-4 autobalance and Pyris 1 DSC analyzer. In this system, Pyris software is used to carry out data analysis on a DEC Venturis 5100 computer. For DSC, an average sample weight of 5–10 mg is heated at 10° C./minute at a 30 psi flow of N$_2$. For TGA, an average sample weight of 10 mg is heated at 20° C./minute under a 8 psi flow of N$_2$. Sessile drop contact angle measurements are obtained with an NRL Goniometer (Rame-hart) using distilled water. Solutions of polymer in methylene chloride (10% wt/volume) are spun-coated onto glass slips, at 5,000 rpm for 30 seconds.

Degradation and drug release profiles of the polymer drug delivery systems of the present invention can also be determined routinely. For these experiments, the polymers are processed into either films, pellets, microspheres, nanospheres or fibers (depending on their properties). After processing, the materials are be characterized to determine if any physicochemical changes have occurred during processing. Uniform processed, weighed, and characterized samples are then degraded in acidic, neutral, and basic phosphate buffer (conditions chosen to simulate physiological range) in triplicate. Periodically the buffer is removed and replaced with fresh media to simulate sink conditions. The spent buffer is analyzed by HPLC to determine the cumulative release of the drug. At defined time periods, samples are removed from the buffer and superficially dried (blotted). They are then weighed to determine the water uptake. At this point, the contact angle (hydrated) is also measured to determine changes in hydrophobicity during degradation. The samples are then thoroughly dried under vacuum and weighed to determine their mass loss. Contact angles (dry) are measured again to determine the hydrophobicity of the dry material, and how it compares to that of the hydrated material. By plotting cumulative release of the degradation products over time, the degradation kinetics can be defined. Wet and dry polymer weights over time indicate if the material is bulk or surface eroding. If there is an increase in water uptake, it can be determined that the polymer is bulk eroding, whereas if there is little or no water uptake the material is considered surface-eroding. By plotting the changes in dry weight versus time, the mass lost by the polymer as it erodes can be determined. This information will give additional insight into how the material is degrading. Changes in molecular weight over time are also examined to bolster the degradation results.

Polyanhydride compounds of the present invention can be isolated by known methods commonly employed in the field of synthetic polymers and used to produce a variety of drug delivery products with valuable physical and chemical properties. Polymeric drug delivery systems comprising the polyanhydride compounds of the invention can be readily processed into pastes or solvent cast to yield films, coatings, microspheres and fibers with different geometric shapes for design of various medical implants, and may also be processed by compression molding and extrusion. Medical implant applications include the use of polyanhydrides to form shaped articles such as vascular grafts and stents, bone plates, sutures, implantable sensors, implantable drug delivery devices, stents for tissue regeneration, and other articles that decompose harmlessly while delivering a selected low molecular weight drug at the site of implantation within a known time period. Drugs linked via these polyanhydrides of the present invention can also be incorporated into oral formulations and into products such as skin moisturizers, cleansers, pads, plasters, lotions, creams, gels, ointments, solutions, shampoos, tanning products and lipsticks for topical application.

The quantity of polymeric drug to be administered to a host which is effective for the selected use can be readily determined by those of ordinary skill in the art without undue experimentation. The quantity essentially corresponds stoichiometrically to the amount of drug which is known to produce an effective treatment for the selected use.

The present invention also relates to methods of using compositions comprising these low molecular weight drugs linked via the polyanhydrides in any application wherein delivery of the low molecular weight drug is desired. Route of delivery is selected in accordance with drug being administered and the condition being treated. For example, compositions of the present invention comprising a polyanhydride of Formula (I) linking a low molecular weight drug such as, for example, amoxicillin or cephalexin can be administered orally or topically to treat bacterial infections. Similarly, compositions of the present invention comprising a polyanhydride of Formula (I) linking a low molecular weight drug such as carbidopa or levodopa can be administered orally to patients suffering from Parkinson's disease to alleviate the symptoms of this disease.

In one embodiment of the present invention, the polyanhydride of Formula (I) is used to link two different low molecular weight drugs into a single polymeric drug delivery system. For example, the polyanhydride of Formula (I) can be used to link a drug molecule of carbidopa with a drug molecule of levodopa so that both drugs can be delivered simultaneously via a single polymeric drug delivery system.

Another embodiment of the present invention includes a method of linking low molecular weight drug molecules containing within their structure one carboxylic acid group and at least one amine, thiol, alcohol or phenol group into polymeric drug delivery systems comprising; (a) protecting the carboxylic acid group of the lowmolecular weight drug molecules; (b) adding to the low molecular weight drug molecules a chlorinated polyanhydride linker of formula (IV)

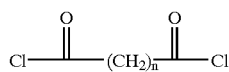

(IV)

wherein n is from 1 to 20, so that drug molecules displace the chlorine groups of the polyanhydride linker of Formula (IV) and bind to the linker via their amine, thiol, alcohol or phenol group; and (c) exposing the linked drug molecules to heat or vacuum so that the protecting groups are removed. In a preferred compound of formula (IV) n is from 6–8.

The linking of a drug in a anhydride polymer of the present invention is shown in the following schemes. The carboxylic acid group of the low molecular weight drug molecule is protected, preferably via acetylation. The protected drug molecules are then exposed to the linker of the linker of formula (IV), optionally in an activated form, e.g., the chlorinated form and bind to the linker ($R^2$) via the amine, thiol, alcohol or phenol groups of the drug molecules. The drug and linker are then exposed to heat and/or vacuum to remove the protecting groups, thereby resulting in a polymeric drug delivery system. The polymers of the invention will have from about 10 to about 30 repeating units.

The linkage of low molecular weight drugs meeting the structural requirements of a single carboxylic acid group and at least one amine, thiol, alcohol or phenol group within its structure are exemplified in the following Examples 1 and 2.

EXAMPLE 1

Synthesis of Amoxicillin Polymer

The linkage of amoxicillin in a polyanhydride of the present invention is shown in the scheme 1. The carboxylic acid group of the low molecular weight drug molecule is protected, preferably via acetylation. The protected drug molecules are then exposed to a chlorinated form of the linker of formula (IV), wherein n is 8. The amine groups from the drug molecules displace the chlorine groups of the diacyl halide Formula (IV) and bind to the linker($R^2$) via the amine, groups of the drug molecules. The linked drug is exposed to heat and/or vacuum to remove the protecting groups, thereby resulting in a polymeric drug delivery system.

Scheme 1

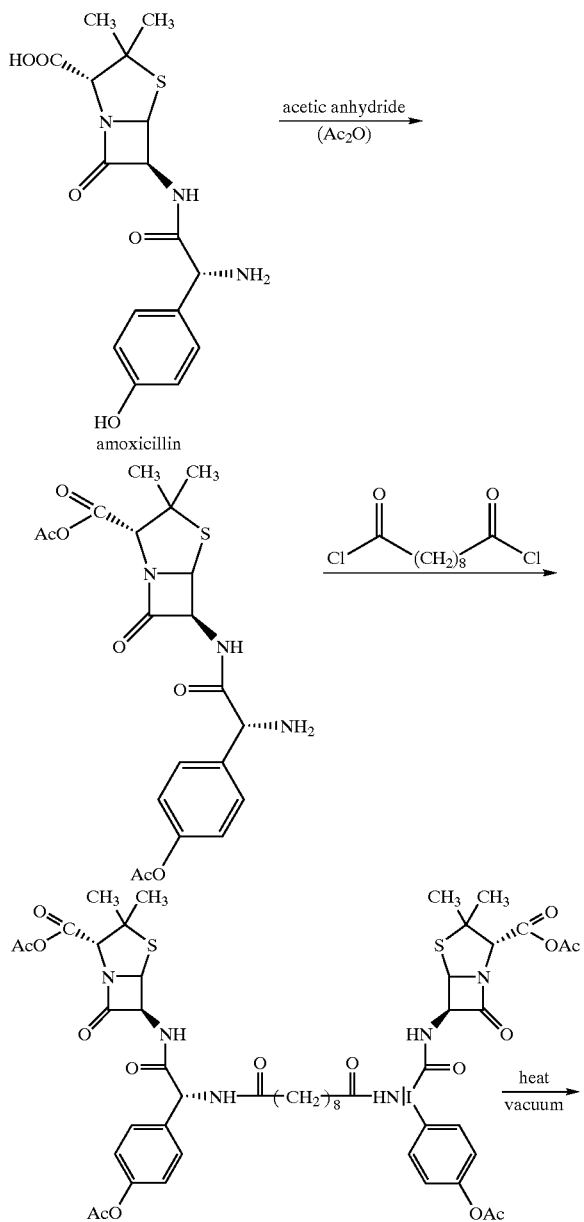

-continued

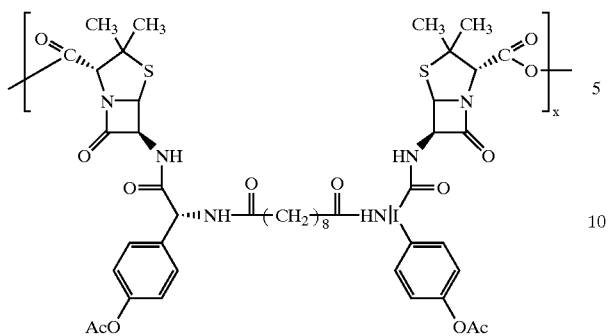

EXAMPLE 2

Synthesis of Cephalexin Polymer

A cephalexin polymer is prepared as depicted in scheme 2. The carboxylic acid group of cephalexin is first protected, for example with a benzylic group. The drug is then linked to sebacoyl chloride (formula (IV) where n is 8). Following this linkage, the protecting groups are removed to produce carboxylic acids which are then acetylated to produce monomer. The monomer is polymerized as a melt.

Scheme 2

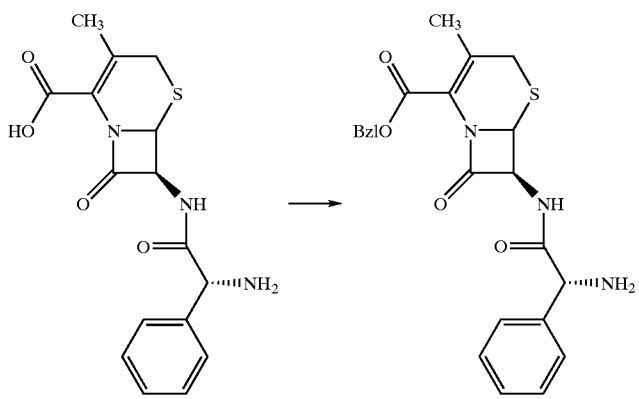

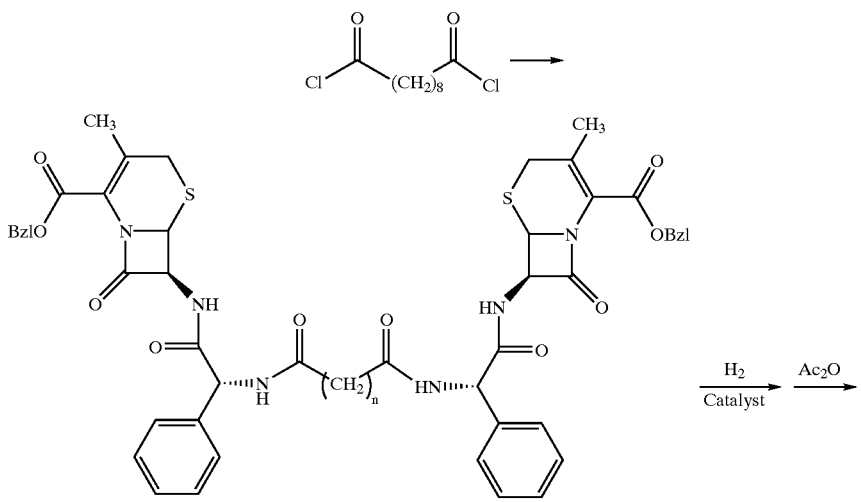

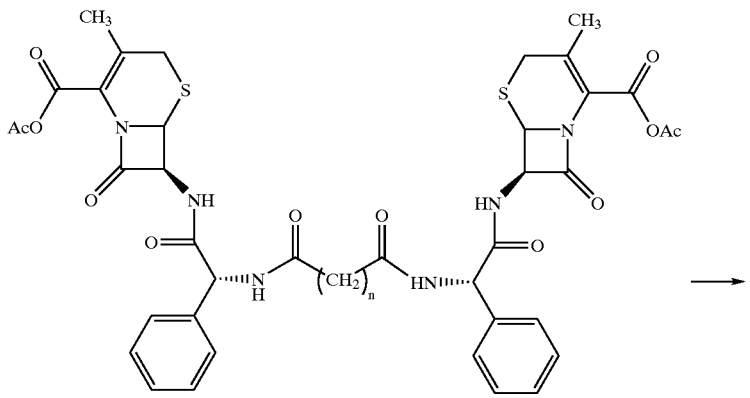

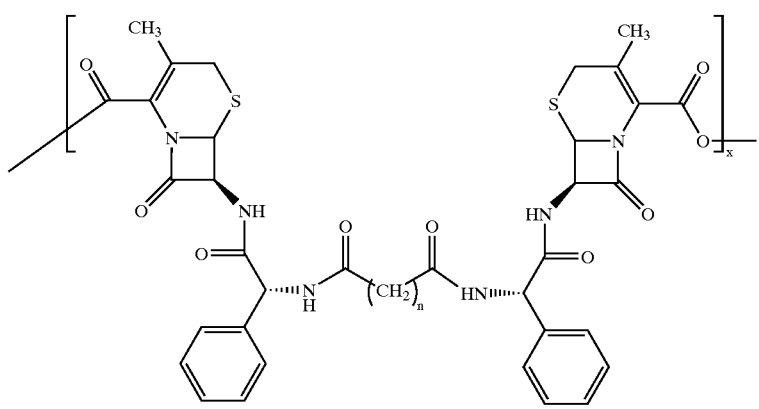

EXAMPLE 3

Other polymeric drug delivery systems can be prepared in accordance with this method via the polyanhydride linker of Formula (I) of the present invention include, but are certainly not limited to, a carbidopa delivery system, a levodopa delivery system and an amtenac delivery system. Homopolymers of the carbidopa and levodopa drug delivery systems are depicted in Formulas (V) and (VI), respectively.

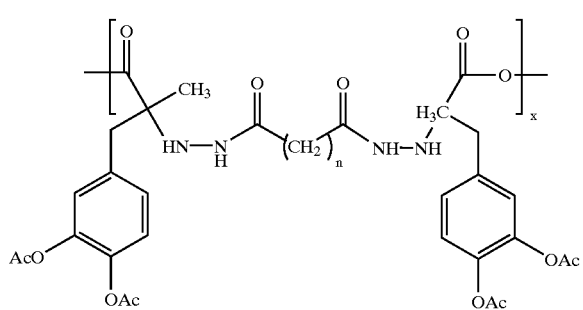

(V)

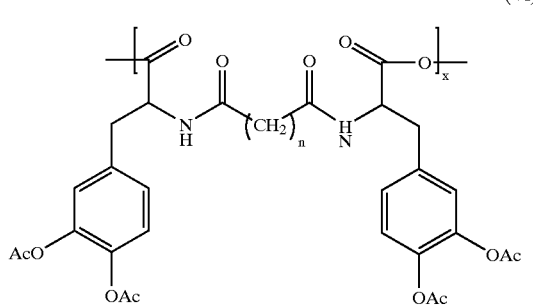

(VI)

While these structures depict homopolymers, copolymers of such drugs can also be prepared routinely based upon the teachings provided herein. Further, polymeric drug delivery systems comprising the polyanhydride of Formula (I) and other drugs meeting the structural requirements, namely one carboxylic acid group, at least one amine, thiol, alcohol or phenol group, and having a molecular weight of approximately 1000 daltons or less can also be routinely prepared via the disclosed methods.

Activity

The ability of a polymer of the invention to produce a given therapeutic effect can be determined using in vitro and in vivo pharmacological models which are well known to the art.

All publications, patents, and patent documents (including the entire contents of U.S. Provisional Patent Application Number 60/220,998, filed Jul. 27, 2000) are incorporated by reference herein, as though individually incorporated by reference. The invention has been described with reference to various specific and preferred embodiments and techniques. However, it should be understood that many variations and modifications may be made while remaining within the spirit and scope of the invention.

What is claimed is:

1. A polymer comprising a backbone, wherein the backbone comprises an anhydride linkage, and wherein the backbone comprises one or more groups that will yield a biologically active compound upon hydrolysis of the polymer; provided that the biologically active compound is not an ortho-hydroxy aryl carboxylic acid: and provided that the biologically active compound is not an alpha-hydroxy carboxylic acid: wherein the biologically active compound is an anti-inflammatory agent, an antibiotic, an anti-fungal agent, an anti-infective, an anti-cancer agent, an anti-thrombotic, an immunomodulator, an antidiabetic agent, an antineoplastic, an antiosteoporotic, an ultraviolet screening agent, or a psychotherapeutic agent.

2. The polymer of claim 1 which comprises one or more units of formula (I) in the backbone:

$$—C(=O)R^1—X—R^2—X—R^1—C(=O)—O—  \quad (I)$$

wherein
each $R^1$ is group that will provide a biologically active compound upon hydrolysis of the polymer; provided that the biologically active compound is not an ortho-hydroxy aryl carboxylic acid
each X is independently an amide linkage, a thioester linkage, or an ester linkage; and
$R^2$ is a linking group.

3. The polymer of claims 1 or 2 wherein the biologically active compound is a non-steroidal anti-inflammatory agent, an antibiotic, an anti-fungal agent, an anti-cancer agent, an anti-thrombotic, or an immunomodulator.

4. The polymer of claims 1 or 2, wherein the biologically active compound is 3-amino-4-hydroxybutyric acid, 6-diazo-5-oxo-L-norleucine, aceclofenac, acediasulfone, alminoprofen, amfenac, amoxicillin, amphotericin B, ampicillin, apalcillin, apicycline, aspoxicillin, azaserine, aztreonam, bambermycin(s), biapenem, bromfenac, bucillamine, bumadizon, candicidin(s), carbenicillin, carprofen, carumonam, carzinophillin A, cefadroxil, cefamandole, cefatrizine, cefbuperazone, cefclidin, cefdinir, cefditoren, cefepime, cefetamet, cefixime, cefmenoxime, cefminox, cefodizime, cefonicid, cefoperazone, cefloranide, cefotaxime, cefotetan, cefotiam, cefozopran, cefpimizole, cefpiramide, cefpirome, cefprozil, cefroxadine, ceftazidime, cefteram, ceftibuten, ceftriaxone, cefuzonam, cephalexin, cephaloglycin, cephalosporin C, cephradine, ciprofloxacin, clinafloxacin, cyclacillin, denopterin, diclofenac, edatrexate, eflomithine, enfenamic acid, enoxacin, epicillin, etodolac, flomoxef, flufenamic acid, grepafloxacin, hetacillin, imipenem, lomefloxacin, lucensomycin, lymecycline, meclofenamic acid, mefenamic acid, melphalan, meropenem, methotrexate, moxalactam, mupirocin, mycophenolic acid, mycophenolic acid, nadifloxacin, natamycin, niflumic acid, norfloxacin, nystatin, oxaceprol, panipenem, pazufloxacin, penicillin N, pipemidic acid, podophyllinic acid 2-ethylhydrazide, procodazole, pteropterin, quinacillin, ritipenem, romurtide, S-adenosylmethionine, salazosulfadimidine, sparfloxacin, streptonigrin, succisulfone, sulfachrysoidine, sulfaloxic acid, teicoplanin, temafloxacin, temocillin, ticarcillin, tigemonam, tolfenamic acid, (N-((5-(((1,4-Dihydro-2-methyl-4-oxo-6-quinazolinyl)methyl)methylamino)-2-thienyl)carbonyl)-L-glutamic acid), tosufloxacin, trovafloxacin, ubenimex or vancomycin.

5. The polymer of claim 3, wherein the anti-bacterial compound is acediasulfone, amfenac, amoxicillin, ampicillin, apalcillin, apicycline, aspoxicillin, aztreonam, bambermycin(s), biapenem, carbenicillin, carumonam, cefadroxil, cefamandole, cefatrizine, cefbuperazone, cefclidin, cefdinir, cefditoren, cefepime, cefetamet, cefixime, cefinenoxime, cefminox, cefodizime, cefonicid, cefoperazone, cefloranide, cefotaxime, cefotetan, cefotiam, cefozopran, cefpimizole, cefpiramide, cefpirome, cefprozil, cefroxadine, ceftazidime, cefteram, ceftibuten, ceftriaxone, cefuzonam, cephalexin, cephaloglycin, cephalosporin C, cephradine, ciprofloxacin, clinafloxacin, cyclacillin, enoxacin, epicillin, flomoxef, grepafloxacin, hetacillin, imipenem, lomefloxacin, lymecycline, meropenem, moxalactam, mupirocin, nadifloxacin, norfloxacin, panipenem, pazufloxacin, penicillin N, pipemidic acid, quinacillin, ritipenem, salazosulfadimidine, sparfloxacin, succisulfone, sulfachrysoidine, sulfaloxic acid, teicoplanin, temafloxacin, temocillin, ticarcillin, tigemonam, tosufloxacin, trovafloxacin, or vancomycin.

6. The polymer of claim 3, wherein the anti-fungal compound is amphotericin B, azaserine, candicidin(s), lucensomycin, natamycin or nystatin.

7. The polymer of claim 3, wherein the anti-cancer compound is 6-diazo-5-oxo-L-norleucine, azaserine, carzinophillin A, denopterin, edatrexate, eflomithine, melphalan, methotrexate, mycophenolic acid, podophyllinic acid 2-ethylhydrazide, pteropterin, streptonigrin, (N-((5-(((1,4-Dihydro-2-methyl-4-oxo-6-quinazolinyl)methyl) methylamino)-2-thienyl)carbonyl)-L-glutamic acid), or, ubenimex.

8. The polymer of claim 3, wherein the immunosuppressive compound is bucillamine, mycophenolic acid, procodazole, romurtide or ubenimex.

9. The polymer of claim 3, wherein the non-steroidal anti-inflammatory compound is 3-amino-4-hydroxybutyric acid, aceclofenac, alminoprofen, bromfenac, bumadizon, carprofen, diclofenac, enfenamic acid, etodolac, flufenamic acid, meclofenamic acid, mefenamic acid, niflumic acid, oxaceprol, S-adenosylmethionine or tolfenamic acid.

10. The polymer of claim 4, wherein the biologically active compound is amoxicillin or cephalexin.

11. The polymer of claim 2, wherein the biologically active compound is carbidopa, or levodopa.

12. The polymer of claim 2 which is a polymer of formula (II) or (III):

$$—C(O)R^1—C(O)O—R^2—O(O)C—R^1—C(O)—O—  \quad (II)$$

$$—C(O)R^1—C(O)O—R^2—O(O)C—R^1—C(O)—O—  \quad (III).$$

13. The polymer of claim 2, wherein $R^2$ is a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—) or (—NR—), and wherein the chain is optionally substituted on carbon with one or more (e.g. 1, 2, 3, or 4) substituents selected from the group consisting of (C$_1$–C$_6$)alkoxy, (C$_3$–C$_6$)cycloalkyl, (C$_1$–C$_6$)alkanoyl, (C$_1$–C$_6$)alkanoyloxy, (C$_1$–C$_6$)alkoxycarbonyl, (C$_1$–C$_6$)alkylthio, azido, cyano, nitro, halo, hydroxy, oxo, carboxy, aryl, aryloxy, heteroaryl, and heteroaryloxy.

14. The polymer of claim 2, wherein R$^2$ is a divalent, branched or unbranched, saturated or unsaturated, hydrocarbon chain, having from 1 to 25 carbon atoms, wherein the chain is optionally substituted on carbon with one or more (e.g. 1, 2, 3, or 4) substituents selected from the group consisting of (C$_1$–C$_6$)alkoxy, (C$_3$–C$_6$)cycloalkyl, (C$_1$–C$_6$)alkanoyl, (C$_1$–C$_6$)alkanoyloxy, (C$_1$–C$_6$)alkoxycarbonyl, (C$_1$–C$_6$)alkylthio, azido, cyano, nitro, halo, hydroxy, oxo, carboxy, aryl, aryloxy, heteroaryl, and heteroaryloxy.

15. The polymer of claim 2, wherein R$^2$ is a peptide.

16. The polymer of claim 2, wherein R$^2$ is an amino acid.

17. The polymer of claim 2, wherein R$^2$ is a divalent, branched or unbranched, saturated or unsaturated, hydrocarbon chain, having from 1 to 25 carbon atoms, wherein one or more (e.g. 1, 2, 3, or 4) of the carbon atoms is optionally replaced by (—O—) or (—NR—).

18. The polymer of claim 2, wherein R$^2$ is a divalent, branched or unbranched, saturated or unsaturated, hydrocarbon chain, having from 3 to 15 carbon atoms, wherein one or more (e.g. 1, 2, 3, or 4) of the carbon atoms is optionally replaced by (—O—) or (—NR—), and wherein the chain is optionally substituted on carbon with one or more (e.g. 1, 2, 3, or 4) substituents selected from the group consisting of (C$_1$–C$_6$)alkoxy, (C$_3$–C$_6$)cycloalkyl, (C$_1$–C$_6$)alkanoyl, (C$_1$–C$_6$)alkanoyloxy, (C$_1$–C$_6$)alkoxycarbonyl, (C$_1$–C$_6$)alkylthio, azido, cyano, nitro, halo, hydroxy, oxo, carboxy, aryl, aryloxy, heteroaryl, and heteroaryloxy.

19. The polymer of claim 2, wherein R$^2$ is a divalent, branched or unbranched, saturated or unsaturated, hydrocarbon chain, having from 3 to 15 carbon atoms, wherein one or more (e.g. 1, 2, 3, or 4) of the carbon atoms is optionally replaced by (—O—) or (—NR—).

20. The polymer of claim 2, wherein R$^2$ is a divalent, branched or unbranched, saturated or unsaturated, hydrocarbon chain, having from 3 to 15 carbon atoms.

21. The polymer of claim 2, wherein R$^2$ is a divalent, branched or unbranched, hydrocarbon chain, having from 3 to 15 carbon atoms.

22. The polymer of claim 2, wherein R$^2$ is a divalent, branched or unbranched, hydrocarbon chain, having from 6 to 10 carbon atoms.

23. The polymer of claim 2, wherein R$^2$ is a divalent hydrocarbon chain having 7, 8, or 9 carbon atoms.

24. The polymer of claim 2, wherein R$^2$ is a divalent hydrocarbon chain having 8 carbon atoms.

25. The polymer of claim 1, further comprising another therapeutic agent dispersed in the matrix of the polymer.

26. The polymer of claim 1, further comprising another therapeutic agent appended to the polymer backbone.

27. A pharmaceutical composition comprising a polymer of claim 1 and a pharmaceutically acceptable carrier.

28. A therapeutic method for treating a disease in an animal comprising administering to an animal in need of such therapy, an effective amount of a polymer of claim 1.

29. A therapeutic method for producing an anti-bacterial effect in an animal comprising administering to an animal in need of such therapy, an effective amount of a polymer of claim 5.

30. A therapeutic method for producing an anti-fungal effect in an animal comprising administering to an animal in need of such therapy, an effective amount of a polymer of claim 6.

31. A therapeutic method for treating cancer comprising administering to an animal in need of such therapy, an effective amount of a polymer of claim 7.

32. A therapeutic method for producing an anti-inflammatory effect in an animal comprising administering to an animal in need of such therapy, an effective amount of a polymer of claim 9.

33. A method of delivering a biologically active compound to a host comprising administering to the host a polymer of claim 1.

* * * * *

UNITED STATES PATENT AND TRADEMARK OFFICE
CERTIFICATE OF CORRECTION

PATENT NO. : 6,613,807 B2
DATED : September 2, 2003
INVENTOR(S) : Kathryn E. Uhrich It is certified that error appears in the above-identified patent and that said Letters Patent is hereby corrected as shown below:

Column 21,
Lines 21 and 23, delete ":" after "acid" and insert -- ; -- therefor.

Column 22,
Line 58, delete "—C(O)R$^1$—C(O)O—R$^2$—O(O)C—R$^1$—C(O)—O— (II)"
and insert -- C(O)R$^1$—OC(O)—R$^2$—(O)CO—R$^1$—C(O)—O— (II) -- therefor.

Signed and Sealed this

Twenty-first Day of September, 2004

JON W. DUDAS
*Director of the United States Patent and Trademark Office*